United States Patent [19]

Bonomini

[11] Patent Number: 4,649,134

[45] Date of Patent: Mar. 10, 1987

[54] PHARMACEUTICAL COMPOSITION CONTAINING DEFIBROTIDE FOR THE TREATMENT OF STATES OF ACUTE RENAL INSUFFICIENCY

[75] Inventor: Vittorio Bonomini, Bologna, Italy

[73] Assignee: Crinos Industria Farmacobiologica SpA, Villa Guardia Como, Italy

[21] Appl. No.: 649,069

[22] Filed: Sep. 10, 1984

[30] Foreign Application Priority Data

Sep. 12, 1983 [IT] Italy ................................ 22856 A/83

[51] Int. Cl.$^4$ .............................................. A61K 31/70
[52] U.S. Cl. ...................................................... 514/44
[58] Field of Search ........................ 536/24, 28; 514/44

[56] References Cited

U.S. PATENT DOCUMENTS 3,770,720 11/1973 Butti et al. .............................. 536/24
3,829,567 8/1974 Butti et al. .............................. 536/24
3,899,481 8/1975 Butti et al. .............................. 536/24

OTHER PUBLICATIONS

Pescador et al, *Thrombosis Research*, vol. 30, pp. 1–11, 1983.
Niada et al, *Pharmacological Research Communications*, vol. 14, No. 10, pp. 949–957, 1982.
*Haemostasis*, "Proceedings of the Defibrotide Symposium", Mar. 1986.
Bonomini et al, *Nephron*, vol. 40, pp. 195–200, 1985.

*Primary Examiner*—Johnnie R. Brown
*Assistant Examiner*—Elli Peselev
*Attorney, Agent, or Firm*—Murray and Whisenhunt

[57] ABSTRACT

The administration of the drug, containing defibrotide as the active ingredient, in the case of acute renal insufficiencies accompanied by a thrombotic microangiopathy, permits the evolution of the clinical situation towards the chronicity to be stopped and, in a number of cases, a complete remission to be obtained.

9 Claims, No Drawings

PHARMACEUTICAL COMPOSITION CONTAINING DEFIBROTIDE FOR THE TREATMENT OF STATES OF ACUTE RENAL INSUFFICIENCY

The present invention relates to a pharmaceutical composition useful for the treatment of forms of acute renal insuficiency. More specifically the composition according to the present invention permits, in the case of acute renal insufficiencies characterized by the presence of thrombotic microangiopathy, not only the evolution of the clinical situation towards the chronicity to be stopped, but also, in a number of cases, a complete remission of the disease to be obtained.

The acute renal insufficiency induced by alteration of the glomerular circuit often does complicate the evolution situation of the following pathologies:

U.E.S. (Uremic-haemolytic syndrome)
Collagenopathies (Panarteritis, Lupus)
Wegener
Schoenlein-Henoch
D.I.C. (Disseminated intravascular coagulation)
Fast evoluting glomerulo nephritis
Thrombotic thrombocytopenic purpura (TPP)

The anatomo-pathologic alterations characterizing these forms, are represented by the formation (as shown by the histological examination) of ialine macrothrombi which occlude the terminal small artheria and glomerular capillar vessels.

Such a condition, known under the name of "thrombotic microangiopathy", represents the most insidious and persistent event.

Particularly the uremic-haemolytic syndrome and the thrombotic thrombocytopenic purpura share several features of the symptomatologic frame amongst which are mycroangiopathic haemolytic anemia, thrombocytopenia and alteration of the renal function.

The appearance of extended anury, hyving hipertension and neurological symptomatology represents an unfavourable prognostic sign both as regards the recovery of the renal functionality and, sometimes, as regards the patient survival.

To date such a type of disease has not found in the present by available therapeutical means something capable of ensuring satisfactory results.

Some of the active principles are hereinafter listed which have been used and/or are used and/or have been suggested for the therapy of the syndrome known under the name of acute renal insufficiency.

(1) Heparin. The known anticoagulating action of such a substance prevents a further evolution of the thrombotic process. However, since it does inhibit some other factors involved in the blood coagulating process, it may induce the appearance of dangerous side effects, among which the most serious is represented by the appearance of hemorrhagies.

(2) Urokinase and streptokinase. These are substances having fibrinolytic action which are prepared, at very high costs, respectively from human urine and from filtrates of cultures of streptococcis (Group C).

The fibrinolytic action is due to the activation of the plasminogen, with consequent formation of a proteolytic enzyme i.e. the plasmine. The use of these substances does not only involve risks of hemorrhagic phenomena which are not controllable and of serious allergic reactions but is also limited only to the phases immediately following the thrombotic occurrence.

(3) Platelet anti-aggregating substances. These products inhibit the further evolution of the thrombus and may prevent subsequent thrombotic occurrences. They present several side effects, mainly in the case of extended therapies, in part depending on the common features of this class of drugs (gastro-intestinal diseases blooding risks) and in part depending on the intrinsic features of the molecule (for instance myelotoxicity of the Ticlopidine).

(4) Cortisonic products. In these pathologies their antidisreactive, antiinflammatory and, in part, immunosuppressing activity is exploited. They present several contra indications and side effects well known in the literature.

(5) Immunodepressing agents. They are mainly used to control the immunitary answer which very often is altered in the patients affected by glomerulopathies.

They request particular cautions owing to their high toxicity (at the level of the medulla ossium, heart, reproduction organs).

Besides the pharmacotherapeutical treatments, other treatments exist which are based on mechanisms having different action, such as the plasma transfusion and the dialysis. In fact, some successful results have been very recently obtained through a plasma tranfusion. The "rationale" of such a therapeutical approach, which is not yet fully clarified, consists in the removal of a toxic factor from the plasma and/or in the affording of a lacking plasmatic factor, which in the normal subjects has a platelet anti-aggregating activity and an inducing activity of prostacycline synthesis.

At present status of knowledge, such a therapeutical approach, which can not be easily carried out awaits further confirmation in the therapy. In turn the dialytic treatment, sometimes used in the acute phase of the disease, does not prevent a chronic renal damage to be developed.

Furthermore, the carring out of such a therapy is reserved to the centers having suitable equipments and specialized personnel.

To date, consequently, no pharmacological or other treatment has achieved the purpose of restoring, at the renal level, the glomerular filtration, by canalyzing again the vessels affected by thrombosis. Consequently, otherwise stated, the therapeutical intervention as carried out to date had as the maximum objective that of stopping the evolution of the disease towards the chronical form.

It has been now found and is the subject of the present invention that by the administration of the defibrotide, namely of the polyanionyc sodium salt of nucleotidic fractions (polydesoxyribonucleotides) having low molecular weight, is capable of stopping the evolution of acute renal insufficiencies towards the chronic form and frequently of determining the functional recovery and the complete remission of the disease.

The defibrotide, (DCI, liste 21, Chronique OMS, 35, 5 suppl. 4 (1981)), is a polydesoxyribonucleotyde (U.S. Pat. No. 3,829,567), prepared through the extraction from animal organs (see U.S. Pat. Nos. 3,770,720 and 3,899,481 which are herein referred to for greater details), devoid of anticoagulating activity and of haemodynamic effects and which presents relevant profibrinolytic and antithrombotic activity under different experimental conditions (Antithrombotic activity of polydeoxyribonucleotides of mammalian origin (Laboratory Code; Fraction P) in experimental animals", VII International Congress on Thrombosis and Haemostasis (London July 15–20, 1979) Abs. No. 1162, Thrombosis and Haemostasis, 42 474,1979 and Pescador R. et al. "Pharmacokinetics of Defibrotide and of its profibrinolytic activity in the rabbit"-Thrombosis Research, 30, 1–11, 1983). From the above properties, however, not only was it unforseable that no one would have even remotely guessed that such an active principle might have the above indicated activity in the case of the acute renal insufficiencies, account being also taken of the fact that in the preceding listing of the active principles to date used or proposed for such type of diseases, some compounds as the urokinase show relevant problems and insufficiencies.

As it is confirmed from the several research works published on defibrotide, such an active principle in practically devoid of toxicity and likewise devoid of unfavourable side effects.

The abovementioned U.S. Pat. Nos. 3,829,567; 3,770,720 and 3,899,481 and hereby incorporated by reference for the disclosure of defibrotide and methods of preparation thereof disclosed therein.

Defibrotide was the subject of in vivo experimental tests in patients. Five patients (3 children and 2 adults) affected by uremyc-haemolytic syndrome or by thrombotic thrombocytopenic purpura were treated. All the patients, who needed the dialytic treatment, at the time of the hospitalization were anuric; the creatinine concentration was of between 5.3 and 8.7 mg/day; the platelet count was low (between 11,000 and 35,000/cubic mm); lastly all the patients had a high circulating level of products of fibrin degradation (FDP). At the time of hospitalization three of them were affected by symptoms of neurologic nature.

The defibrotide was administered in vials of 2.5 ml content, containing 200 mg of defibrotide, through intravenous infusion at the daily dosage of 10 mg/kg. The treatment was started at 16–28 hours after the hospitalization and continued on the average for 14 days.

In all patients a fast diminution of the fibrin degration products in circulation as well as an increase of the platelet number were found.

The diuresis increased and the creatinine concentration in the serum was reduced in four patients, with a total recovery of the renal functionality in a time varying from 12 to 47 days.

The administration of the defibrotide furthermore involved the disappearance of the symptoms of neurologic type.

Like experiments carried out on patients affected by medical nephropathies gave essentially like results. However, in the cases of nephropathies with long course, the treatment was continued by oral route by means of tablets with the specific purpose of preventing a chronicity status from being set out.

From the in vivo experimental results as above reported the importance clearly appears of the pharmaceutical composition according to the invention in the therapy of a syndrome which generally brings the patient, if not to the death, at least to a constant dependency on a dialysis treatment.

It is furthermore to be pointed out that such an activity of the defibrotide might not be supposed on the basis of the to date known properties of such an active substance since, as previoulsy mentioned, the treatment of states of acute renal insufficiencies with anti-thrombotic and fibrinolytic agents never gave place not only to a recovery of the renal functionality but not even to a stopping of the evolution towards the chronic state.

The amount of defibrotide to be administered to a given patient will vary according to the specific conditions involved, including the specific conditions of acute renal insufficiency, as well as the size and general health of the patient. Normally a daily dosage of defibrotide in the range of 400 to 800 mg will be used for an adult patient, generally corresponding to a daily dosage of about 6 to 12 mg per kg of body weight.

It is lastly to be observed that the preparation of the pharmaceutical compositions according to the invention provides both oral forms (capsules, tablets) and injectable forms (vials for parenteral and intravenous use), as prepared with the known galenic techniques and by means of the usual vehicles, excipients, solvents, etc. The pharmaceutical compositions of the present invention are usually prepared following conventional methods for administration in a pharmaceutically suitable form. Compositions in the form of solid oral forms may contain in addition to the active compounds diluents such as lactose, dextrose, saccarose and other sugars, cellulose, mais, starch and other vegetable starches such as corn starch and potato starch, lubricants such as silica, talc, stearic acid, magnesium or calcium stearate and/or polyethylene glycols, binding agents such as vegetable starches, arabic gums, gelatin, methylcellulose, carboxymethyl cellulose, polyvinyl pyrrolidone, and the like, disaggregating agents such as starch, alginic acid, alginates, sodium starch glycolate, and in general non-toxic and pharmacologically inactive substances commonly used in pharmaceutical formulations. The solutions for intravenous injections or infusions may contain as a carrier sterile water or preferably sterile aqueous isotonic saline solutions.

EXAMPLE 1

Pharmaceutical composition for injectable use: 2.5 ml vials

| | |
|---|---|
| defibrotide | mg 200 |
| trisodium citrate dihydrate | mg 25 |
| methyl p-hydroxybenzoate | mg 3.13 |
| propyl p-hydroxybenzoate | mg 0.62 |
| water for injectable preparations | enough to 2.5 ml |

EXAMPLE 2

Pharmaceutical composition for oral use

| Capsules (content) | | | |
|---|---|---|---|
| defibrotide | 200 | 100 | 50 |
| lactose | 56.75 | 87.6 | 137.6 |
| colloidal silica | 0.65 | 0.5 | 0.5 |
| magnesium stearate | 2.64 | 1.9 | 1.9 |
| Tablets | | | |
| defibrotide | 200 | | |
| mannitol | 117.2 | | |
| mais starch | 9.94 | | |
| magnesium stearate | 2.82 | | |

The amounts are expressed in mg.

What is claimed is:

1. A method of treating acute renal insufficiencies in a patient in need of such treatment, said method comprising administering to said patient an effective amount of defibrotide.

2. Method of claim 1, wherein said patient is effected by uremic-haemolytic syndrome.

3. Method of claim 1, wherein said patient is effected by thrombotic thrombocytopenic purpura.

4. Method of claim 1, wherein the amount of said defibrotide administered to said patient is about 6 to about 12 mg per kg of body weight.

5. Method of claim 1, wherein a daily dosage of about 400 to about 800 mg of defibrotide is administered to said patient.

6. Method of claim 1, wherein said defibrotide is administered orally.

7. Method of claim 1, wherein said defibrotide is administered in the form of a capsule or tablet.

8. Method of claim 1, wherein said defibrotide is administered by intramuscular injection.

9. Method of claim 1, wherein said defibrotide is administered intravenously.